United States Patent [19]
Graham et al.

[11] Patent Number: 5,236,966
[45] Date of Patent: Aug. 17, 1993

[54] POLYMERIC MATERIALS

[75] Inventors: Neil B. Graham, Glasgow; Christopher R. Moran, Ayrshire, both of Wales

[73] Assignee: British Technology Group Limited, London, England

[21] Appl. No.: 828,940

[22] PCT Filed: Aug. 14, 1990

[86] PCT No.: PCT/GB90/01279
§ 371 Date: Feb. 6, 1992
§ 102(e) Date: Feb. 6, 1992

[87] PCT Pub. No.: WO91/02763
PCT Pub. Date: Mar. 7, 1991

[30] Foreign Application Priority Data
Aug. 15, 1989 [GB] United Kingdom ................ 8918589

[51] Int. Cl.$^5$ .............................................. C08G 18/14
[52] U.S. Cl. ...................................... 521/163; 528/68; 528/76; 528/77; 524/590; 524/591; 524/839
[58] Field of Search ................... 521/163; 528/68, 76, 528/77; 524/590, 591, 839

[56] References Cited

U.S. PATENT DOCUMENTS 4,130,517 12/1978 Lundberg et al. ............. 260/29.2 N

FOREIGN PATENT DOCUMENTS 1127082 4/1962 Fed. Rep. of Germany .
1566595 3/1969 France .
1551620 8/1979 United Kingdom .
2047093A 11/1980 United Kingdom .

Primary Examiner—Maurice J. Welsh
Attorney, Agent, or Firm—Nixon & Vanderhye

[57] ABSTRACT

Linear chain extended poly(alkylene oxides) having at least a portion of hydrophobic hydrogen bonding chain extending groups are soluble in at least one solvent and swellable in water. The chain extending groups preferably comprise a urea linkage and can be produced by the reaction of an amine with an isocyanate. The extended polymers and their solutions may readily be fabricated into controlled release compositions, e.g. for the release of pharmaceuticals.

30 Claims, No Drawings

POLYMERIC MATERIALS

This invention relates to linear chain extended polymers, to processes for the production and to their utility inter alia in controlled release compositions.

Chemically cross-linked polymeric hydrogel compositions comprising polyalkylene glycols and their use in controlled release compositions have been described e.g. in British Patents 2047093 and 2047094. Whilst these compositions exhibit highly desirable release properties the cross-linked nature of these polymers means that their fabrication into useful devices is complicated by the fact that the hydrogel can only be formed by casting the reactant mixture. Although simple shapes can be produced relatively easily the fabrication of more complex shapes will normally require a machining step.

The cross-linking of these compositions has been found to be essential for the production of essentially water insoluble hydrogals since the omission of the cross-linking agent leads to the production of urethane chain-extended polyalkylene glycols which are not water insoluble and which have insufficient mechanical strength to be useful.

British patent 1551620 describes linear block polymers which are useful as components of controlled release compositions wherein the polymers are amphipathic materials comprising alternating blocks of hydrophilic and hydrophobic regions. The polymers preferably comprise at least 30% by weight of hydrophilic regions. Yui et al. in Journal of Controlled Release 6 1987 p329-342 describe multi-block copolymers consisting of sequences of soft and hard segments which form a microphase separated structure composed of hard segment clusters and surrounding soft segment matrices. the actual materials reported being segmented polyether-poly(urethane-urea)s.

We have now discovered a novel class of chain extended linear poly(alkylene oxide) hydrogels which are swellable rather than soluble in water and soluble in an organic solvent medium. The incorporation of a proportion of chain extending groups which comprise a hydrophobic hydrogen bonding group has surprisingly been found to insolubilise the polyalkylene glycols which would otherwise be soluble in water.

As a result the novel polymeric hydrogels of this invention can be manufactured in or dissolved in a solvent to form novel solutions which can be utilised for coating, dipping, rolling or spraying to form surface coatings or complex shapes and as thermoplastics in conventional manufacturing procedures, for example compression, injection or extrusion molding processes which enables the novel hydrogels to be produced in a variety of forms both quickly and cheaply. The novel hydrogels can also be prepared as emulsions in water or in mixtures of suitable solvents and water.

From one aspect this invention provides a solvent soluble linear chain extended polymer which comprises hydrophilic poly(alkylene oxide) segments which is characterised in that the hydrophilic segments are connected by a hydrophobic hydrogen bonding chain extending group.

In this specification the term "solvent soluble polymer" is used to mean a polymer which is soluble rather than swellable in at least one organic solvent medium. The solvent (or mixture of solvents) is preferably a polar organic solvent such as a chlorinated hydrocarbon solvent e.g. chloroform or an alcohol such as methanol.

In accordance with this invention the hydrophilic segments comprise poly(alkylene oxide) and most preferably poly(ethylene oxide) residues. These residues may comprise a minor amount of an additional component either as a random or block copolymer with the poly(alkylene oxide). However the nature and amount of such a component should not render the segment hydrophobic or having hydrophobic/hydrophilic nature. Generally the proportion of such a component will comprise no more than 20% and preferably no more than 10% by weight of the hydrophilic segment. Examples of monomers which may be used as such a component include epihalohydrins. cyclic mono or poly ethers such as oxetane. tetrahydrofuran, dihydrofuran, dihydropyran, dioxolane and trioxane and N(epoxy substituted) heterocyclic compounds such as N-[2,3-epoxypropyl]-pyrolidone. In a particularly preferred embodiment the hydrophilic segment comprises a poly(ethylene oxide) comprising up to 25% and preferably up to 20% by weight of an alkylene oxide which is selected from the group comprising propylene oxide. 1,2, epoxybutane and 2,3, epoxybutane either as a random or a block copolymer with the poly(ethylene oxide). Hydrophilic segments which comprise a random or block copolymer of ethylene oxide with up to 25% of propylene oxide are especially preferred.

In accordance with a particularly preferred aspect of this invention the hydrophilic segments comprise homopolymeric poly-(ethylene oxide) which may have a number average molecular weight from 500 to 8,000 or even higher, (for example 20,000) suitably from 2,000 to 7,000. Those segments which exhibit crystallinity are preferred insofar as the property may permit convenient purification techniques to be practised and lead to higher strength polymers in the dry state.

The preferred hydrophobic hydrogen bonding chain extending groups which may form part of the polymers of this invention are those which comprise at least one urea linkage as part of their molecular structure. The chain extending group will be hydrophobic in nature. In general the preferred chain extending group will comprise a hydrocarbyl residue having from 2 to 20 carbon atoms optionally interrupted by hetero-atoms.

The polymers of this invention preferably incorporate at least one chain extending group for each hydrophilic segment. The proportion of urea linkages incorporated into these groups will preferably be such that they comprise from 0.1 to 10.0% by weight typically from 0.5 to 5.0% by weight of the total weight of the polymer. The balance of the chain extending groups needed to provide the preferred stoichiometry may take the form of groups which do not comprise a urea linkage.

A convenient reaction which may be utilised to produce the polymers of the invention wherein the chain extending group comprises a urea linkage is that between an amine functional group and an isocyanate functional group. Where the hydrophilic poly(alkylene oxide) segment takes the form of a poly(alkylene glycol) this reaction may conveniently be utilised by reacting the poly(alkylene glycol) with a di-isocyanate in the presence of a diamine. The resultant polymers comprise hydrophobic chain extending groups having the formula I

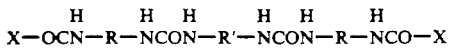

$$\text{X—OCN—R—NCON—R'—NCON—R—NCO—X} \quad \text{I}$$

wherein X represents the poly(alkylene oxide) segment, R represents a hydrocarbyl residue derived from the di-isocyanate and R' represents a hydrocarbyl residue derived from the diamine.

An alternative group of polymers are those which may be produced by the conversion of a controlled proportion of the poly(alkylene glycol) to an amine derivative having an amine function at each end of the segment. Such a conversion may be effected using any of the known techniques of synthetic organic chemistry. The amino derivative may then be reacted with a di-isocyanate to produce a hydrophobic chain extended group having the formula II

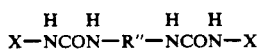

$$\text{X—NCON—R''—NCON—X} \quad \text{II}$$

wherein X represents the poly(alkylene oxide) segment and R" represents a hydrocarbyl residue derived from the di-isocyanate.

The isocyanate which may be employed in these reactions may be an aromatic, aliphatic or cycloaliphatic di-isocyanate or a bis-isocyanate terminated prepolymer. The use of aliphatic or cycloaliphatic di-isocyanates comprising from 2 to 20 carbon atoms per molecule is preferred. Examples of useful di-isocyanates include 1,6 hexamethyl di-isocyanate, isophorone di-isocyanate, 4,4' dicyclohexyl methane di-isocyanate, cyclohexylene 1,2 and 1,4 di-isocyanates and 4,4 diphenyl methane di-isocyanate.

The reaction with the poly(alkylene glycol) may utilise any aromatic, aliphatic or cycloaliphatic diamine which is compatible with the polymerisation system. Any of the diamines which can be produced by the hydrolysis of any of the di-isocyanates referred to above may be utilised. Preferably the diamine comprises two primary amine functions and does not comprise any secondary amine functions. The presence of tertiary amino groups may be desirable in some instances. Examples of preferred diamines include bis-4-amino phenyl methane, bis-4-amino cyclohexyl methane and 1,6 hexamethylene diamine.

A preferred form of di-isocyanate prepolymer which may be reacted with the amino derivative of the poly(alkylene glycol) are prepolymers formed by the reaction of two molar proportions of a di-isocyanate with one molar proportion of a poly(alkylene glycol). Any of the poly(alkylene glycols) and any of the di-isocyanates hereinbefore described may be utilised to produce such a prepolymer. The nature of the residue R" in formula ii will correspond to the composition of that prepolymer.

In all these synthesis the proportion of urea linkages in the final polymer may be controlled by control of the proportion of amine groups introduced as reactants. Where the amine is to be generated in situ by hydrolysis of a di-isocyanate the quantity of water employed should be carefully controlled so as to avoid the formation of polymers having a significant degree of crosslinking.

In accordance with a further preferred feature of this invention, it is found that polymers of the invention with advantageous mechanical properties, for example enhanced toughness, are formed when the di-isocyanate is present in stoichiometric excess, preferably a small stoichiometric excess such as from 0.5% to 10%, preferably from 1% to 5%, by weight of the di-isocyanate above the stoichiometric requirement of one functional group per active hydrogen atom in the hydrophilic segments. Higher stoichiometric excess may result in the undesirable formation of insoluble polymer.

The polymers of the present invention may be prepared by forming a homogeneous melt or a solution of the hydrophilic segment and then adding the necessary agent, or reagents optionally with heating and the addition of catalyst. The chain extension may be most conveniently performed in the absence of solvents but solvents may be desirable when using high molecular weight starting materials such as polyethylene glycols having number average molecular weights of greater than say 8000 or where the object is to produce a solution of the polymeric material in a solvent. In the case of di-isocyanate chain extending agents Lewis acid species such as ferric chloride are useful catalysts particularly when the products are intended for medical or pharmaceutical applications although other conventional catalysts known to be effective in urethane group formation such as stannous octoate, dibutyl tin dilaurate or tertiary amines may be employed.

It is desirable that the hydrogels are swellable often above 10×, for example from 20× to 70× or more, even above 100× by weight in aqueous media. It is also preferred that the glass transition temperature is below the service temperature (that is, the temperature of the polymer in use) and, preferably, below ambient temperature. that is the polymer is elastomeric.

The polymers of the invention may be formed as blocks, foam, sheet, film, fiber or powder.

This invention also provides a controlled release composition which comprises a polymer as herein defined having incorporated therein an active substance, particularly a biologically active substance, for example a medication system. By "medication system" is meant any physiologically active substance or substances which it is desired, either by way of prophylaxis or therapy, to provide in vivo.

The present invention is of broad applicability in the formulation of active substances, particularly, but not exclusively, biologically active substances releasable at a controlled rate. Examples of classes of biologically active substances which may be incorporated in the controlled release compositions cf the present invention include flavorings, pharmaceuticals, bacteriostats, viruscides, pesticides such as insecticides, nematicides, molluscicides and larvicides, herbicides, fungicides, algaecides, topical or dermatological agents, antifoulants for marine growth prevention, proteins, for example enzymes, peptides, microbiological and plant hydroculture salts and nutrients and preservatives, veterinary trace metal formulations, and other growth promoting factors used in animal husbandry; for example, anti-anaemia preparation and anabolic steroids. Of particular interest are compositions of the present invention comprising, as biologically active substance, at least one pharmaceutical.

The compositions of this invention thus find wide application in medical and surgical, including veterinary, contexts and in horticulture and agriculture as well as outside these areas.

The active substance will possess some degree of water solubility although this may be relatively small.

The active substances may be incorporated into the polymer after this has been formed into an appropriate shape, in which case the active substance will be soluble in the solvent used to swell the polymeric hydrogel. However, it is an advantage of the present invention that the polymeric hydrogel may be dissolved in an organic solvent, usually a polar organic solvent such as chloroform, ethanol/chloroform, methanol, ethanol, nitrobenzene, methyl benzoate, butyrolactone, tetrahydrofuran or benzyl alcohol in which the active substance is also soluble or dispersible; and the solution or dispersion containing the active substance can then be solvent cast. This also allows the polymers to be used as coatings on granules or on tablets providing excellent release profiles or used as film or pouches thus providing essentially constant release devices. Alternatively the active material may be incorporated into a hollow envelope of the hydrogel which can be sealed by the application of solvent to the adjoining edges. The novel devices may also be formed by dry mixing the active material with the hydrogel polymers and forming a device by compression molding, injection molding or extrusion processes.

Using dispersions or drug solutions in the solution of polymer the mixed system is able to be applied as a film or coating. Thus such a system can be applied as topical coatings on humans, animals or inert surfaces. Direct applicaton of liquid by brushing, wiping or aerosol is also possible.

Specific classes of medication system which may be used in a controlled release composition of the invention include abortificients such as prostaglandins, hypnotics, sedatives, tranquilizers, anti-pyretics, anti-inflammatory agents, antihistamines, antitussives, anticonvulsants, muscle relaxants, anti-tumor agents, for example those for the treatment of malignant neoplasia, local anaesthetics, anti-Parkinson agents. topical or dermatological agents, diuretics, for example those containing potassium, such as potassium iodide, preparations for the treatment of mental illness, for example preparations containing lithium for use in the treatment of manic depression or containing prostaglandins for the treatment of schizophrenia, anti-spasmodics, anti-ulcer agents, preparations containing various substances for the treatment of infection by pathogens including anti-fungal agents, for example metronidazole, anti-parasitic agents and other anti-microbials, anti-malarials, cardiovascular agents, preparations containing hormones, for example androgenic; estrogenic and progestational hormones, notably steroids such as oestradiol, sympathomimetic agents, hypoglycaemic agents, contraceptives, nutritional agents, preparations containing enzymes of various types of activity for example chymotrypsin, preparations containing analgesics, for example aspirin, and agents with many other types of action including nematocides and other agents of veterinary application. Mixtures of active substances may be incorporated into the controlled release compositions.

The controlled release compositions of this invention may be used as a contraceptive composition suitably containing, as active subtances, at least one natural or synthetic steroid sex hormone for example an oestrogen or progestogen. Suitable progestogens include the natural progesterone and its synthetic analogues, including 11-dehydro-progesterone, delalutin, 21-fluoro-17-acetoxy-6-methylprogesterone, medroxyprogesterone acetate, megestrol acetate, chlormadinone acetate, ethisterone, dimethisterone, A-norprogesterone, 19-norprogesterone, 21-norprogesterone, normethandone, norethynodrel, norethindrone and its acetate, D1- and D-norgestrel, norgestrienone, ethynodiol diacetate, lynstrenol, ethynylestradiol, retroprogesterone, dydrogesterone, norvinodrel, quingestranol acetate, norethisterone and its acetate and oenanthate, anagesterone acetate, medrogestone, clomagestone, allyl estrenol and cingestol, preferably progesterone. Suitably oestrogens include the natural $\beta$-oestradiol and its synthetic analogues, principally ethinyloestradiol or mestranol, preferably $\beta$-oestradiol.

The controlled release compositions of this invention are also useful in the treatment of diabetes and pernicious anaemia where, for example, the controlled release of insulin and cobalamin, respectively, may be utilized.

Moreover, the controlled release compositions of this invention are particularly suited to treatment, both prophylactic and therapeutic, of tropical diseases; for example, malaria, leprosy, schistosomiasis and clonorchiasis. Examples of drugs which can be used as biologically active substances in sustained release compositions of this invention for the treatment of these and other tropical diseases include quinine, sulphanamides, rifamcin, clofazimine, thiambutosine, chlor-phenyl derivatives, chlorguamide, cycloguanil, pyrimethamine, sulpha-diazine, trimethoprim, quinoline derivatives such as pamaquine, chloroquine, pentaquine, primaquine and amodiquine, pararosaniline, sulphamethizole, quinacrine, dapsone, sodium sulphoxone, sulphetrone, sodium hydnocarpate and sodium chaulmoograte. Drugs of particular effectiveness are cycloguanil, pyrimethamine and sulphadiazine.

The controlled release compositions of this invention are also very well suited to veterinary applications. Examples include preparations of antibiotics for general antibacterial activity and also in the treatment of anaplasmosis in cattle; preparations for provision of a wide spectrum of activity against both ectoparasites, for example termites and endoparasites including arthropods, arrested larvae stages of nematodes, lungworms and general strongyles: these may comprise avermectins; preparations for provision of activity against tremotode, cestode and roundworm infections: these may comprise amoscanate and praziquantel; preparations for provision of activity against theileria in cattle: these may comprise biologically active nephthoquinones such as menoctone; preparations for provision of activity against babesiosis in cattle, horses and dogs: these may comprise berenil, amidocarb and diampron; preparations for provision of activity against liver fluke in sheep and cattle and against Haemonchus species: these may comprise closantel. The controlled release compositions of this invention are also well suited for bio-medical applications by formation into films, tubes, stents and catheters. Such compositions can usefully incorporate biocides to render the surfaces difficult to colonise by cells which may cause occlusion. By contrast they are bio and haemo compatible and may in many situations be used without such additives.

The invention is illustrated by the following Examples.

EXAMPLE 1

A number of linear polyurethaneurea (PUU) hydrogels were prepared using hydrophilic poly(ethylene glycol), (PEG), homopolymers of different molecular weights.

[MW PEG1610, PEG3330, PEG5830],
4,4'- Diaminodiphenylmethane;
Dicyclohexylmethane 4,4' - Diisocyanate
and Anhydrous Ferric Chloride as a catalyst.

The poly(ethylene glycols) were dried by bubbling dry nitrogen through the molten polymer at 100° C. under vacuum for 3 hours.

The dry PEG was weighed accurately into a beaker and the desired amount of diamine added. The beaker was placed in an oven at 95° C. until the diamine had completely dissolved in the PEG Anhydrous FeCl$_3$ (0.02% by wgt of final polymer) was then added and the beaker returned to the oven to allow the catalyst to dissolve in the mixture. The di-isocyanate was added from a burette (5% excess on stoichiometry of the reactants) and the reaction mixture stirred vigorously until homogeneous before being returned to the oven to equilibrate at 95° C. for 5 minutes. After further stirring the reacting melt was poured into polypropylene bottles preheated to 95° C. The bottles were capped and returned to the oven where the reaction proceeded at 95° C. for 20 hours. On cooling the bottles were cut open and the polymer blocks removed. The PUU's were then dissolved in methanol and cast into films by solvent evaporation.

The compositions of the polymers which were made are set out in the following tables.

| NUMBER OF MOLES | | | WEIGHT PERCENTAGE | | |
|---|---|---|---|---|---|
| | DPDA | Di-iso-cyanate | | DPDA | Di-isocyanate |
| PEG 5830 | | | PEG 5830 | | |
| 1 | 0.384 | 1.453 | 92.72 | 1.21 | 6.07 |
| PEG 3330 | | | PEG 3330 | | |
| 1 | 0.227 | 1.288 | 89.68 | 1.21 | 9.11 |
| 1 | 0.384 | 1.453 | 87.92 | 2.01 | 10.07 |
| PEG 1610 | | | PEG 1610 | | |
| 1 | 0.118 | 1.174 | 82.92 | 1.21 | 15.87 |
| 1 | 0.384 | 1.453 | 77.87 | 3.68 | 18.45 |
| 1 | 0.500 | 1.575 | 75.85 | 4.87 | 19.48 |
| 1 | 0.750 | 1.838 | 71.84 | 6.64 | 21.52 |

All formulations have an excess of 5% of the diisocyanate on the stoichiometric requirement.

The catalyst concentration was 0.02% by weight FeCl$_3$ of the final polymer.

For the PUU based on PEG 5830 any increase in the amount of diamine employed produced an insoluble cross-linked polymer. For the PUU's based on PEG 3330 and PEG 1610 the proportion of diamine was increased until this point was reached. The mechanical strength of swollen films derived from these PUU's increased as the proportion of diamine increased.

We claim:

1. A solvent soluble linear chain extended polymer which comprises hydrophilic (polyalkylene oxide) segments connected by a hydrophobic hydrogen bonding chain extending group comprising at least one urea linkage as part of its molecular structure, said urea groups comprising from 0.1 to 5.0% by weight of the total weight of the polymer.

2. A polymer according to claim 1 wherein the hydrophilic segment is a poly(ethylene oxide) segment.

3. A polymer according to claim 2 wherein poly(ethylene oxide) segment comprises a homopolymeric poly(ethylene oxide) having a number average molecular weight of from 500 to 20,000.

4. A polymer according to claim 3 wherein the poly(ethylene oxide) has a number average molecular weight of from 2,000 to 9,000.

5. A polymer according to claim 1 wherein the polymer comprises units of the formula

wherein X represents a hydrophilic poly(alkylene oxide) segment, R and R' which may be the same or different represent hydrocarbyl groups comprising from 2 to 20 carbon atoms.

6. A polymer according to claim 1 wherein the polymer comprises units of the formula

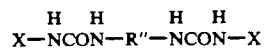

wherein X represents a hydrophilic poly(alkylene oxide) segment and R" represents hydrocarbyl group comprising from 2 to 20 carbon atoms.

7. A polymer according to claim 5 wherein R, R' and R" represents an aromatic, aliphatic or cycloaliphatic group.

8. A polymer according to claim 7 wherein R, R' and R" are selected from the group consisting of hexamethylene, isophorone, 4,4' dicyclohexyl methane, 1,2 and 1,4 cyclohexylene and 4,4' diphenyl methane groups.

9. A polymer according to claim 5 wherein R and R' are identical.

10. A polymer according to claim 6 wherein R" represents a group having the formula

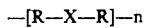

wherein R represents a hydrocarbyl group having from 2 to 20 carbon atoms, X represents a poly(alkylene oxide) group and n is an integer having a value of at least 1.

11. A polymer according to claim 10 wherein R represents a hexamethylene, isophorone, 4,4' dicyclohexyl methane, 1,2 and 1,4 cyclohexylene or 4,4' diphenyl methane group.

12. A process for the preparation of a polymer according to claim 1 which comprises reacting a poly(alkylene glycol) with a di-isocyanate R(NCO)$_2$ in the presence of a diamine R'(NH$_2$)$_2$, wherein R and R' which may be the same or different represent hydrocarbyl groups comprising from 2 to 20 carbon atoms.

13. A process according to claim 12 wherein the diamine has the formula R'(NH$_2$)$_2$ and is generated in situ by the hydrolysis of di-isocyanate.

14. A processfor the preparation of a polymer according to claim 1 which comprises a diamine terminated poly(alkylene oxide) with a di-isocyanate R(NCO)$_2$, wherein R is a hydrocarbyl group comprising from 2 to 20 carbon atoms.

15. A process according to claim 12 which is carried out in the absence of a solvent.

16. A process according to claim 12 wherein the reaction is carried out in the presence of a quantity of a di-isocyanate R(NCO)$_2$ so as to satisfy the stoichiometric requirement of one functional group per active hydrogen atom in the hydrophilic segments.

17. A process according to claim 16 wherein diisocyanate is present in a quantity so as to provide an excess of from 0.5 to 10.0% above the stoichiometric requirement.

18. A solvent soluble linear chain extended polymer whenever produced by a process according to claim 12.

19. A controlled release composition comprising a polymer according to claim 1 in an admixture with an active substance.

20. A composition according to claim 19 wherein the active substance is a biologically active substance.

21. A composition according to claim 20 wherein the active substance is one which is physiologically active in man.

22. A composition according to claim 19 wherein the polymer is in solution.

23. A composition according to claim 22 wherein the active substance is dissolved in the solution.

24. A composition according to claim 22 wherein the active substance is dispersed in the polymer solution.

25. A process for the production of a controlled release composition according to any of claim 19 wherein the active material is dry mixed with the polymer and the composition formed by a compression molding, injection molding or extrusion step.

26. A solution of a polymer according to claim 1.

27. A solution of a polymer produced by a process according to claim 12.

28. An aqueous emulsion of a polymer according to claim 1.

29. An aqueous emulsion of a polymer produced by a process according to claim 12.

30. A controlled release composition comprising a polymer produced by a process according to claim 12 in admixture with an active substance.

* * * * *